United States Patent

Goto et al.

[11] Patent Number: 5,883,933
[45] Date of Patent: Mar. 16, 1999

[54] METHOD AND APPARATUS FOR DISPLAYING THREE-DIMENSIONAL IMAGE

[75] Inventors: Yoshihiro Goto, Katsushika-ku; Hisako Nakamura, Abiko; Tomohiro Nagao, Kashiwa, all of Japan

[73] Assignee: Hitachi Medical Corporation, Tokyo, Japan

[21] Appl. No.: 813,362

[22] Filed: Mar. 7, 1997

[30] Foreign Application Priority Data

Mar. 29, 1996 [JP] Japan .................................. 8-076933

[51] Int. Cl.⁶ ............................... A61B 6/02; A61B 1/00
[52] U.S. Cl. ............................. 378/62; 378/4; 378/901; 600/410
[58] Field of Search .............................. 378/4, 8, 62, 98, 378/901; 395/119, 120; 600/410, 416

[56] References Cited

U.S. PATENT DOCUMENTS 5,611,025  3/1997  Lorensen et al. ...................... 395/119
5,694,530  12/1997 Goto ....................................... 395/119

FOREIGN PATENT DOCUMENTS 0 492 897 A2   7/1992   European Pat. Off. .
7-210704       8/1995   Japan .
8-16813        1/1996   Japan .
7-296184       11/1997  Japan .

*Primary Examiner*—David P. Porta
*Assistant Examiner*—David Vernon Bruce
*Attorney, Agent, or Firm*—Oliff & Berridge, PLC

[57] ABSTRACT

A three-dimensional image is displayed on a display in a central projection method based upon a viewpoint which is placed at the inside of an object and a line of sight. In this case, a plurality of tomographic images interposed between the viewpoint and a projection plane are sequentially arranged and displayed on a display screen. Polygon visual field frames are formed at points of intersection of projection lines forming a polygon pyramid and each tomographic image, and the visual field frames are displayed on the display screen. Thereby, the position of the viewpoint and the line of sight with respect to the currently-displayed three-dimensional image showing the inside of the object can be easily detected, and the part of the object which is being displayed can be easily recognized.

58 Claims, 9 Drawing Sheets

F I G. 5
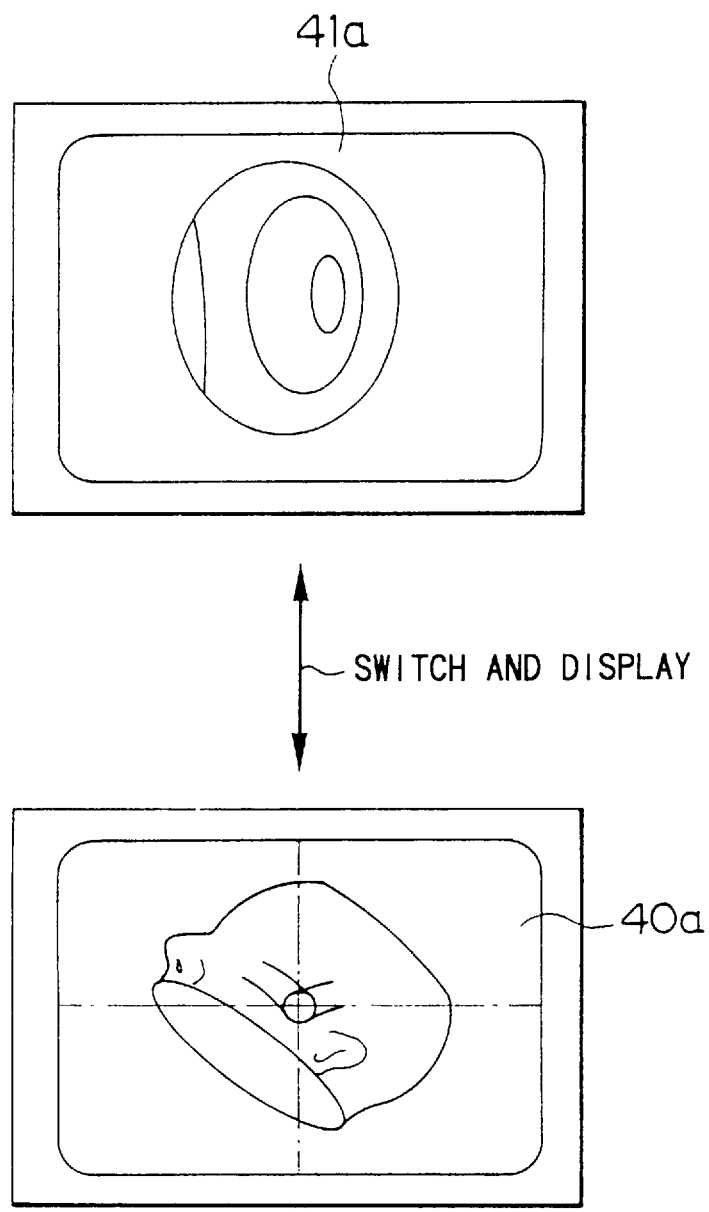

F I G. 8
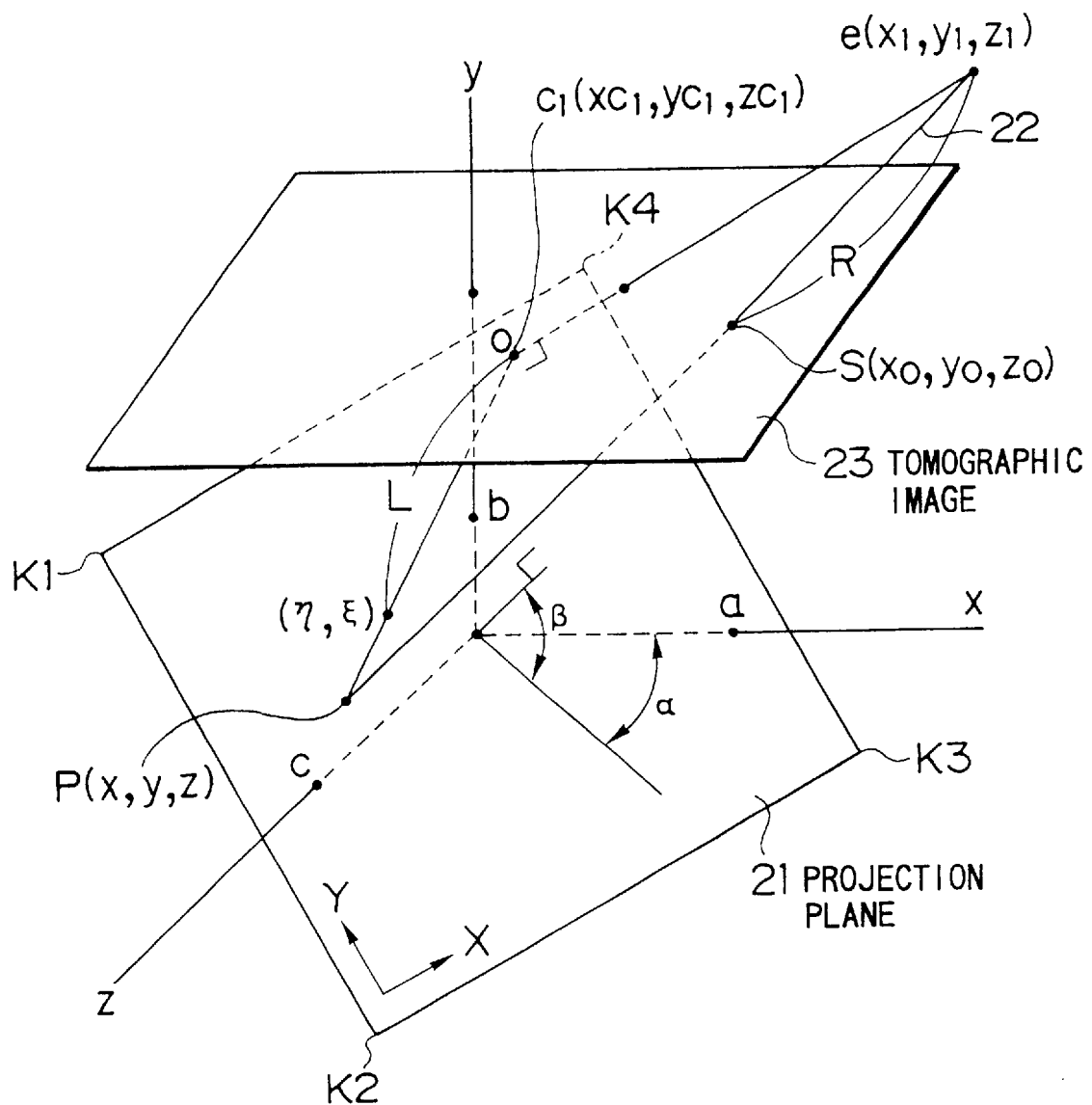

F I G. 9
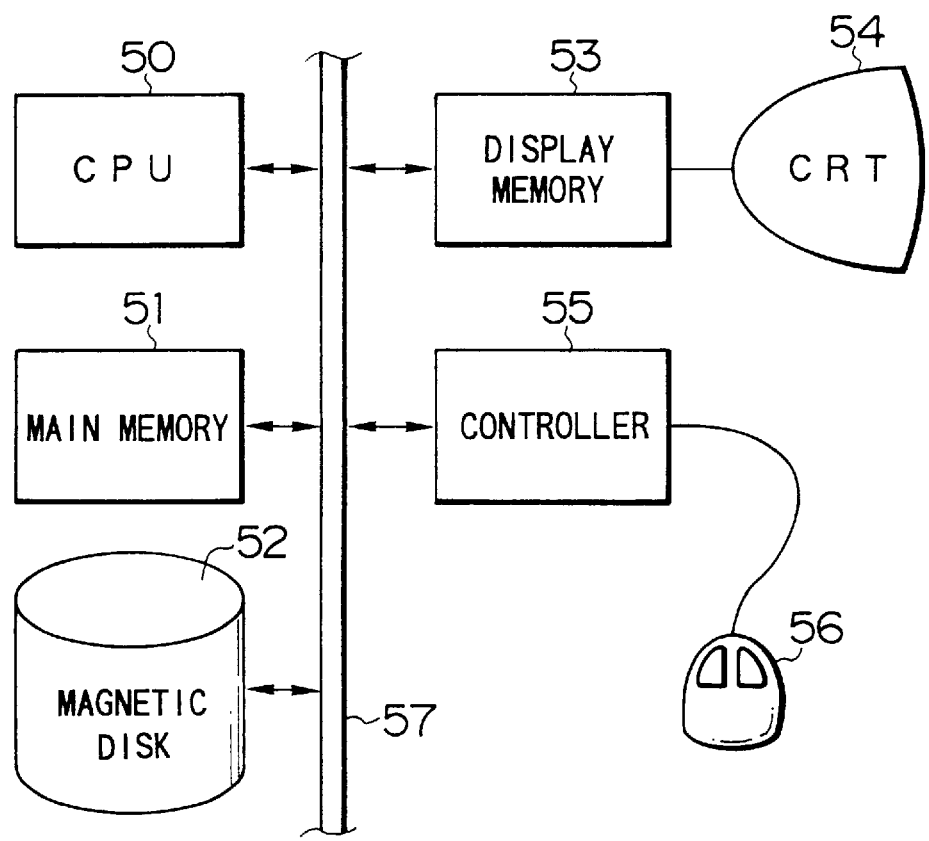

METHOD AND APPARATUS FOR DISPLAYING THREE-DIMENSIONAL IMAGE

BACKGROUND OF THE INVENTION

1. Field of the Invention

The present invention relates generally to a method and apparatus for displaying a three-dimensional image, and more particularly, to a method and apparatus for displaying a three-dimensional image as if the inside of an object was observed under an endoscope.

2. Description of the Related Art

There are a variety of medical images such as an X-ray Computerized Tomography (CT) image, a Magnetic Resonance Imaging (MRI) image, and an ultrasonic tomographic image. In order to obtain a three-dimensional image, the X-ray CT images are stacked slice by slice. Because the MRI image can be measured three-dimensionally, the three-dimensional original image can be obtained by arranging the MRI images.

In a central projection method, a three-dimensional original image interposed between a viewpoint and a projection plane is projected onto the projection plane as if the inside of an object was observed from the viewpoint. In the central projection method, the viewpoint is neither a plane nor a line but a point. The three-dimensional original image interposed between the viewpoint and the projection plane is projected onto the projection plane, with the viewpoint being the center. For example, in order to obtain the three-dimensional original image showing the inside of an intestine, a viewpoint is placed at the inside of the intestine. Then the line of sight is turned from the viewpoint toward the inside of the intestine, so that the inside of the intestine can be observed. In this case, the image is displayed as if the inside of the intestines was observed under an endoscope. The applicant of the present application has already disclosed the central projection method in Japanese Patent Provisional Publication Nos. 7-210704, 7-296184, and 8-16813.

In the central projection method according to the above-mentioned publications, when the viewpoint is placed in an organ, the image shows only one part of the organ. Thus, this central projection method has such a disadvantage that which part of the organ is displayed cannot be easily recognized.

SUMMARY OF THE INVENTION

Accordingly, an object of the invention is to provide a method and apparatus for displaying a three-dimensional image, in which a part of an object shown by the currently-displayed image can be easily recognized.

In order to achieve the above-mentioned object, the present invention comprises: a first image constructing means for constructing a first image of the three-dimensional image, the first image including the three-dimensional image projected on a projection plane from a viewpoint, a line of sight extending from the viewpoint toward the projection plane, and a first plurality of tomographic images; a second image constructing means for constructing a second image, the second image including a second plurality of tomographic images that include the first plurality of tomographic images, the second plurality of tomographic images being sequentially arranged in the second image; and an image displaying means for displaying at least one of the first and second images.

According to the present invention, the first image constructing means constructs the first image showing a three-dimensional image which is obtained by seeing the object from the inside, and the first image is displayed on the screen. At the same time, the second image constructing means constructs the second image by sequentially arranging a plurality of tomographic images interposed between the viewpoint of the first image and the projection plane, and adding information relating to the position of the viewpoint and/or the line of sight to the sequentially-arranged tomographic images. The first and second images are displayed on the screen at the same time, or the first and second images are switched back and forth when they are displayed.

Furthermore, in order to achieve the above-mentioned object, the present invention comprises the steps of: forming a first image, the first image including the three-dimensional image projected onto a projection plane from a viewpoint, a line of sight extending from the viewpoint toward the projection plane, and a first plurality of tomographic images; forming a second image, the second image including a second plurality of tomographic images that include the first plurality of tomographic images, the second plurality of tomographic images being sequentially arranged in the second image; and displaying at least one of the first and second images.

In accordance with the present invention, the first image constructing means constructs the first image showing the three-dimensional image obtained by seeing the object from the inside, and the first image is displayed on the screen. The second image constructing means constructs the second image showing the three-dimensional image of the whole object. The first and second images are displayed on the screen at the same time, or the first and second images are switched to be displayed on the screen.

Thus, the viewpoint and the line of sight of the currently-displayed three-dimensional image can be easily detected, and the part of the object shown by the three-dimensional image can be easily recognized.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 5 is a view explaining that the three-dimensional image showing the inside of an object and the three-dimensional image showing the whole object which is observed from the viewpoint moving backward are switched to be displayed;

FIG. 8 is a view showing the coordinate transformation in the central projecting method in the case where the viewpoint, the tomographic image and the projection plane have more complex relation; and FIG. 9 is a view showing an example of hardware structure realizing the present invention.

DETAILED DESCRIPTION OF THE PREFERRED EMBODIMENTS

Embodiments of the present invention will be described with reference to the drawings.

An explanation will hereunder be given about the coordinate transformation in the central projection method in a method of constructing a three-dimensional image. When each tomographic image is projected onto a projection plane in the central projection method, coordinates of pixels on each tomographic image are transformed into coordinates on the projection plane as described below.

Figure 6:
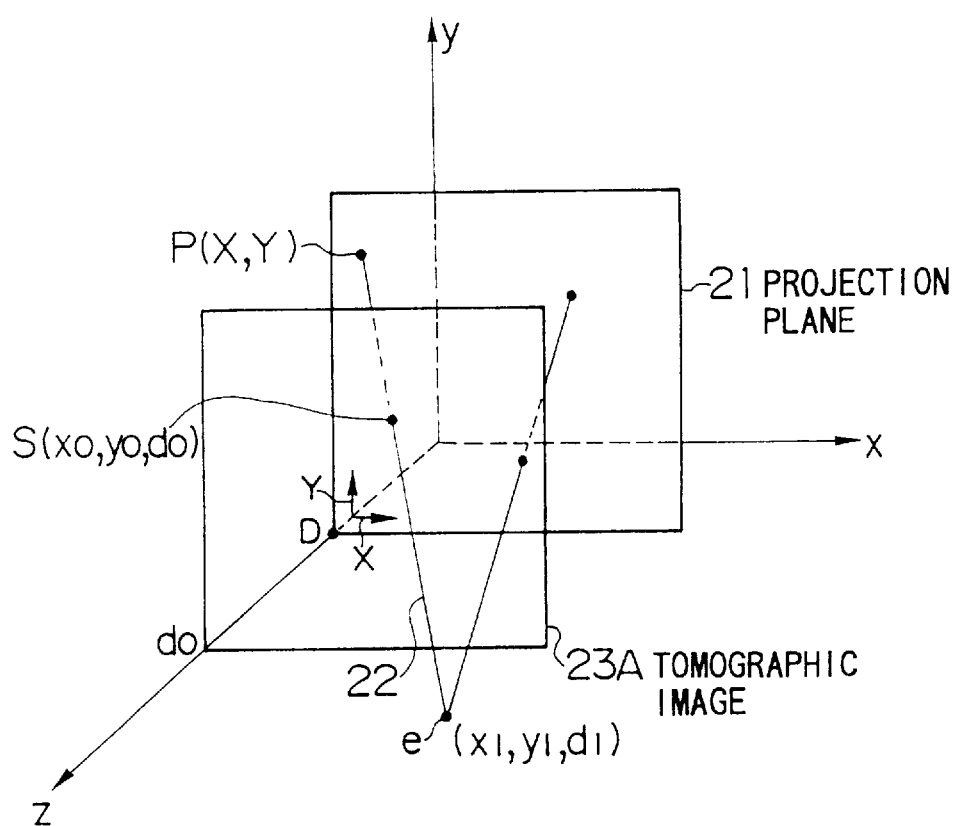
FIG. 6 is a view explaining that coordinates of pixels on the tomographic image are transformed into the coordinates on a projection plane in a method of constructing a three-dimensional image.

In an example shown in FIG. 6, a coordinate system is taken so that the projection plane is parallel with the tomographic image plane and parallel with the x-y plane for simplification of description.

In FIG. 6, $\underline{x}$, $\underline{y}$ and $\underline{z}$ axes represent coordinate axes in a three-dimensional coordinate system (x, y, z); point $\underline{e}$ ($x_1$, $y_1$, $d_1$) represents the position of a viewpoint $\underline{e}$; point P (X, Y) represents a point on the projection plane (equivalent to a display screen) 21; and point S ($x_0$, $y_0$, $d_0$) represents a point of intersection of the tomographic image 23A and a line 22 connecting the point $\underline{e}$ ($x_1$, $y_1$, $d_1$) and the point P (X, Y).

Further, D represents a position (on the $\underline{z}$ axis) of the projection plane 21, which can be set freely.

Further, $d_0$ represents a position (on the $\underline{z}$ axis) of the tomographic image 23A, which is determined at the time of measurement.

Further, $d_1$ represents a $\underline{z}$ coordinate of the viewpoint $\underline{e}$.

According to the above definition, the following equations hold.

$$X = \{(D-d_1)/(d_0-d_1)\} \times (x_0 - x_1) + x_1 \quad (1)$$

$$Y = \{(D-d_1)/(d_0-d_1)\} \times (y_0 - y_1) + y_1 \quad (2)$$

$$x_0 = \{(d_0-d_1)/(D-d_1)\} \times (X - x_1) + x_1 \quad (3)$$

$$y_0 = \{(d_0-d_1)/(D-d_1)\} \times (Y - y_1) + y_1 \quad (4)$$

When the projected image is expressed in 512 pixels by 512 pixels on the display screen (not shown) equivalent to the projection plane 21, each of X and Y takes values of −256 to +256. On the tomographic image 23A at $d_0$, $x_0$ and $y_0$ are determined correspondingly to a pair of X and Y in accordance with the above equations (3) and (4), so that the points to be projected can be determined. Because there are a plurality of tomographic images 23A and accordingly $d_0$ takes a plurality of values, a plurality of points $x_0$ and $y_0$ to be projected are determined correspondingly to one pair of X and Y.

Figure 7:
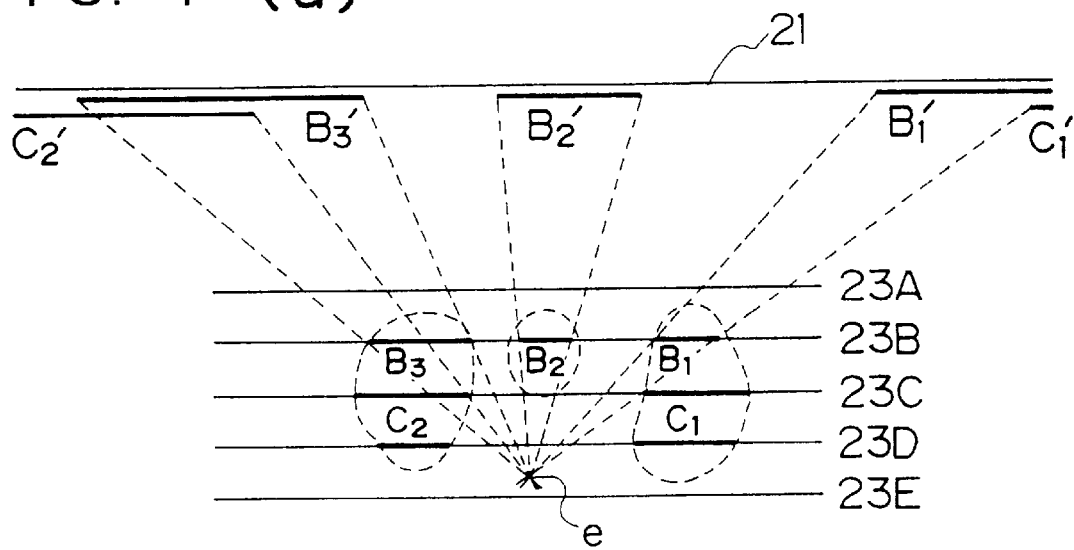
FIGS. 7(a) and 7(b) are views explaining that coordinates of pixels on the tomographic image are transformed into the coordinates on the projection plane on which a plurality of tomographic images are projected.
Figure 7:
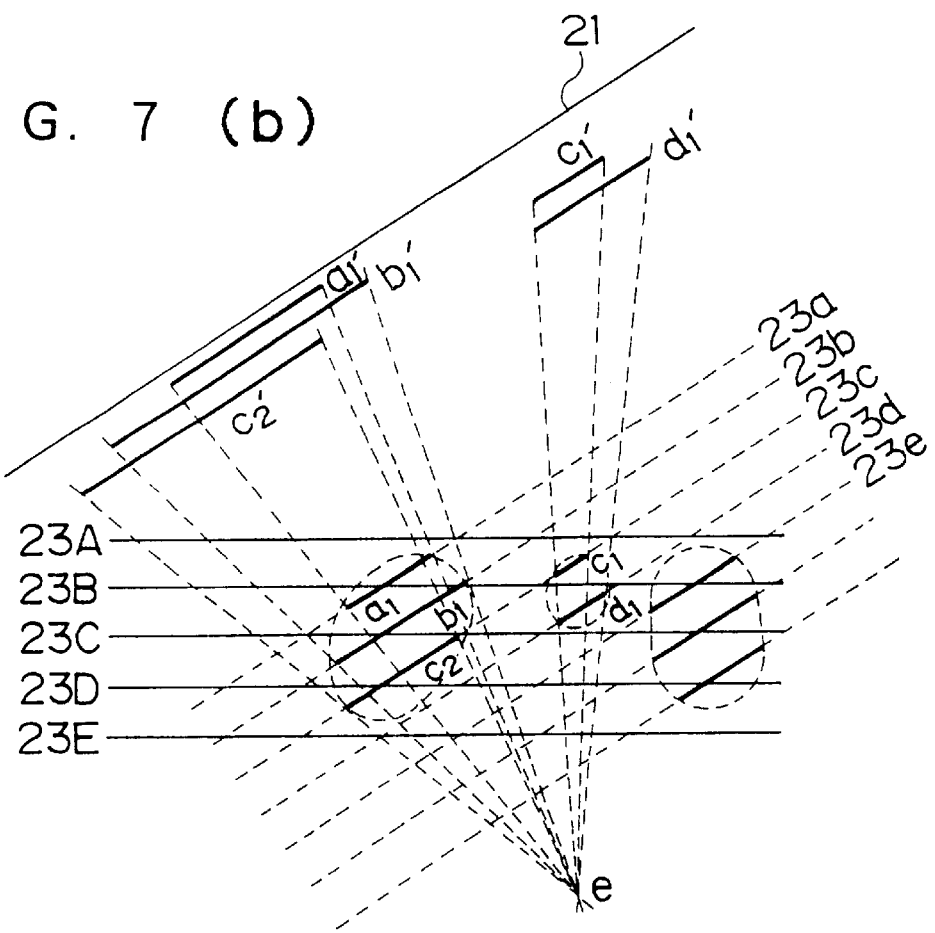

FIG. 7(a) is a view taken in the direction of the $\underline{y}$ axis in the case where tomographic images 23B, 23C, 23D and 23E other than the tomographic image 23A are provided in the same coordinate system. In FIG. 7(a), the tomographic images 23A to 23E are tomographic images obtained at regular intervals in the same direction by measuring the same object (though illustrated example shows the case where the tomographic images are obtained at regular intervals, it is not necessarily so). On the tomographic image 23B, regions $B_1$, $B_2$ and $B_3$ of internal organs are written emphatically. If the regions $B_1$, $B_2$ and $B_3$ of internal organs are projected onto the projection plane 21, then regions $B_1'$, $B_2'$ and $B_3'$ are formed. Similarly, if regions $C_1$ and $C_2$ of internal organs on the tomographic image 23C are projected onto the projection plane 21, then regions $C_1'$ and $C_2'$ are formed.

To obtain a three-dimensional effect, projection data (here $B_1'$, $B_2'$, $B_3'$; $C_1'$, $C_2'$) are written in a display memory (not shown) so that projection data farther from the viewpoint $\underline{e}$ are first written and then nearer projection data are overwritten. Accordingly, here, projection data $B_1'$, $B_2'$ and $B_3'$ are first written, and then the projection data $C_1'$ and $C_2'$ are overwritten, because the projection data $C_1$ and $C_2$ are farther from the viewpoint $\underline{e}$ than the projection data $B_1$, $B_2$ and $B_3$. In order to simplify the explanation about the sequence of the projection data $B_1'$, $B_2'$, $B_3'$, $C_1'$ and $C_2'$ to be written in the display memory, the projection data $B_1'$, $B_2'$, $B_3'$, $C_1'$ and $C_2'$ are shown in FIG. 7(a) as if they were separated from the projection plane 21. That is, in practice, the projection data $B_1'$, $B_2'$ and $B_3'$ written first and the projection data $C_1'$ and $C_2'$ overwritten are projected onto the projection plane 21.

FIG. 7(b) shows a more generalized example than FIG. 7(a), that is, FIG. 7(b) shows the case where the projection plane is not parallel with the tomographic image planes. In this case, tomographic images 23a, 23b, 23c ... parallel with the projection plane 21 are generated by interpolation on the basis of the tomographic images 23A, 23B, 23C .... Other conditions are the same as those in FIG. 5A. In FIG. 7(b), $a_1'$, $b_1'$, $c_1'$, $c_2'$, and $d_1'$ represent the projection data of regions $a_1$, $b_1$, $c_1$, $c_2$, and $d_1$ of internal organs on the tomographic images 23a, 23b, 23c, and 23d generated by interpolation.

FIG. 8 is a view for explaining coordinate transformation in the central projection method in the case where the viewpoint, the tomographic images and the projection plane have more complex positional relations. FIG. 8 shows that projection of point S ($x_0$, $y_0$, $z_0$) on the tomographic image 23 onto the projection plane 21 results in point P (x, y, z) on the projection plane 21.

In FIG. 8, in order to project the tomographic image 23 onto the projection plane 21 in the central projection method, coordinates of pixels of the tomographic image 23 are transformed into coordinates on the projection plane 21 as described hereinbelow.

Here, $\underline{a}$ represents a point of intersection of the $\underline{x}$ axis and the projection plane 21, $\underline{b}$ represents a point of intersection of the $\underline{y}$ axis and the projection plane 21, and $\underline{c}$ represents a point of intersection of the $\underline{z}$ axis and the projection plane 21.

Further, $\alpha$ represents an angle between a line obtained by projecting a perpendicular from the origin to the projection plane 21 onto the x-z plane and the $\underline{z}$ axis, $\beta$ represents an angle between the perpendicular and the x-z plane, point e ($x_1$, $y_1$, $z_1$) represents a position of the viewpoint $\underline{e}$, point P (x, y, z) represents a point on the projection plane 21 (equivalent to the display screen), point S ($x_0$, $y_0$, $z_0$) represents a point of intersection of a line connecting the point $\underline{e}$ ($x_1$, $y_1$, $z_1$) and the point P (x, y, z) and the tomographic image 23, and point $c_1$ represents a point of intersection of a perpendicular from the viewpoint $\underline{e}$ ($x_1$, $y_1$, $z_1$) to the projection plane 21 and the projection plane 21.

In the aforementioned definition, the following equations hold.

First, the projection plane 21 is given by the equation:

$$(x/a)+(y/b)+(z/c)=1 \qquad (5)$$

Further, a line 22 connecting the point $\underline{e}$ ($x_1$, $y_1$, $z_1$) and the point P (x, y, z) is given by the equation:

$$(x_0-x)/(x_1-x)=(y_0-y)/(y_1-y)=(z_0-z)/(z_1-z) \qquad (6)$$

Since the projection plane 21 is drawn through the point $C_1$ ($x_{c1}$, $y_{c1}$, $z_{c1}$), the point (x, y, z) on the projection plane 23 is given by the following equations:

$$z=[X \cdot k_1-Y \cdot k_2-y_{c1} k_3-\{(c_i-k_3-z_{c1})/b_i\}+\{(a_i \cdot k_3 \cdot X)/(b_i \cos \alpha)\}$$
$$-\{(a_i \cdot k_3 \cdot X_{c1})/b_i\}]/[1-\{(c_i \cdot k_3)/b_i\}+\{(a_i \cdot k_3 \cdot \sin \alpha)/(b_i \cos \alpha\}] \qquad (7)$$

$$x=(X-z \cdot \sin \alpha)/\cos \alpha \qquad (8)$$

$$y[y_{c1}+\{-c_i \cdot (z-z_{c1})-a_i \cdot (x-x_{c1})\}]/b_i \qquad (9)$$

in which $k_1=\sin \alpha$, $k_2=\cos \alpha/\sin \beta$, $k_3=\cos \alpha \cdot \cos \beta/\sin \beta$, $a_i=1/a$, $b_i=1/b$ and $c_i=1/c$ Here, the aforementioned point $C_1$ ($x_{c1}$, $y_{c1}$, $z_{c1}$) may be given by the following equations:

$$z_{c1}=z_1 \pm [h/\text{sqrt}\{1+(c^2/a^2)+(c^2/b^2)\}](\text{where "--" in "}z_1 \pm \text{" is valid in the case of } z_0 < z_{c1}) \qquad (10)$$

$$x_{c1}=x_1+\{c \cdot (z_1-z_{c1})/a\} \qquad (11)$$

$$y_{c1}=y_1+\{c \cdot (z_1-z_{c1})/b\} \qquad (12)$$

in which $\underline{h}$ represents the length of the perpendicular from the viewpoint $\underline{e}$ ($x_1$, $y_1$, $z_1$) to the projection plane 21.

When the projected image is expressed in 512 pixels by 512 pixels on the display screen (not shown) equivalent to the projection plane 21, each of X and Y takes values of −256 to +256. Values of $\underline{x}$ and $\underline{y}$ are determined correspondingly to the respective values of X and Y in accordance with the above equations (7), (8) and (9). Because $x_1$, $y_1$ and $z_1$ of the point $\underline{e}$ are given freely, coordinates $x_0$ and $z_0$ of the pixel point S on the tomographic image $Y_0=d_0$ are determined in accordance with the following equations (13) and (14).

$$x_0=\{(d_0-y)/(y_1-y)\} \times (x_1-x)+x \qquad (13)$$

$$z_0=\{(d_0-y)/(y_1-y)\} \times (z_1-z)+z \qquad (14)$$

Because $d_0$ takes a plurality of values correspondingly to the plurality of tomographic images, a plurality of points $x_0$ and $y_0$ to be projected are determined correspondingly to a pair of X and Y.

In FIG. 8, R represents a distance from the viewpoint $\underline{e}$ to the point S. In the case where a depth image (which will be described later) is to be obtained, R is a parameter for obtaining the pixel value (luminance) of the point P.

A depth method, a volume rendering method, etc. are used for shading the image. In the depth method for example, the image is shaded according to the distance R from each pixel on the tomographic image 23 to the viewpoint $\underline{e}$. The longer the distance R is, the darker the shaded image becomes. The pixel value at the point P is proportional to a value which is obtained by subtracting R from a maximum pixel value $R_{max}$ which is set in advance.

The above-described coordinate transformation is performed with respect to all points on the projection plane 21 equivalent to the display screen. The coordinate transformation is also performed with respect to all tomographic images 23.

The coordinate transformation may be performed for the already-constructed three-dimensional image or for each tomographic image before the construction of the image.

FIG. 9 is a block diagram illustrating an example of hardware structure realizing the present invention. In FIG. 9, reference numeral 50 designates a central processing unit (CPU); 51, a main memory; 52, a magnetic disk; 53, a display memory; and 55, a mouse controller. The above components are connected to a common bus 57. The magnetic disk 52 contains a plurality of tomographic images, a program for executing the arithmetic operation program for executing the method of the present invention, and the like.

The CPU 50 reads the plurality of tomographic images and the programs; executes the program by using the main memory 51; and forms a three-dimensional image. Then the CPU feeds the results of the operation to the display memory 53 to display the results on a CRT monitor 54.

For example, as described later, the CPU 50 reads out CT data from the magnetic disk 52 in accordance with a viewpoint placed in the inside of the object and a line of sight from the viewpoint, and forms a three-dimensional image, which is shaded and projected on the projection plane in the central projection method in which the viewpoint is the origin.

The CPU 50 also forms images for indicating the position of the viewpoint and the line of sight of the above-mentioned three-dimensional image. Then, the CPU 50 synthesizes or switches the image data, and outputs the image data to the display memory 53, and displays the images on the CRT monitor 54.

A mouse 56 connected to the mouse controller 55 is used to set the position of the viewpoint, or the like, for constructing the three-dimensional image.

Figure 1:
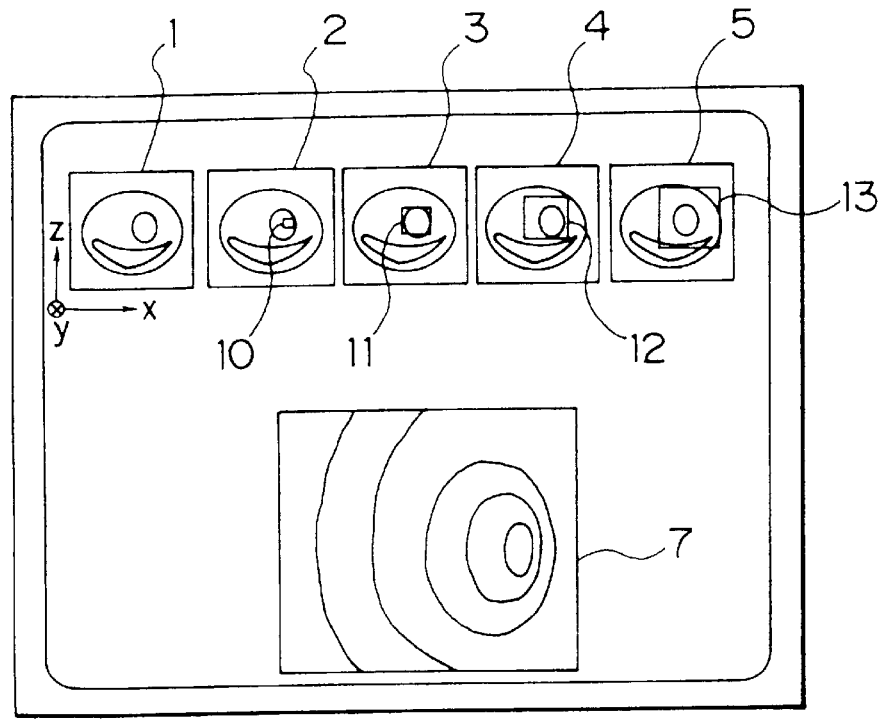
FIGS. 1(a) and 1(b) are views showing a relationship between a three-dimensional image and a visual field (visual field frame) displayed on a tomographic image.
Figure 1:
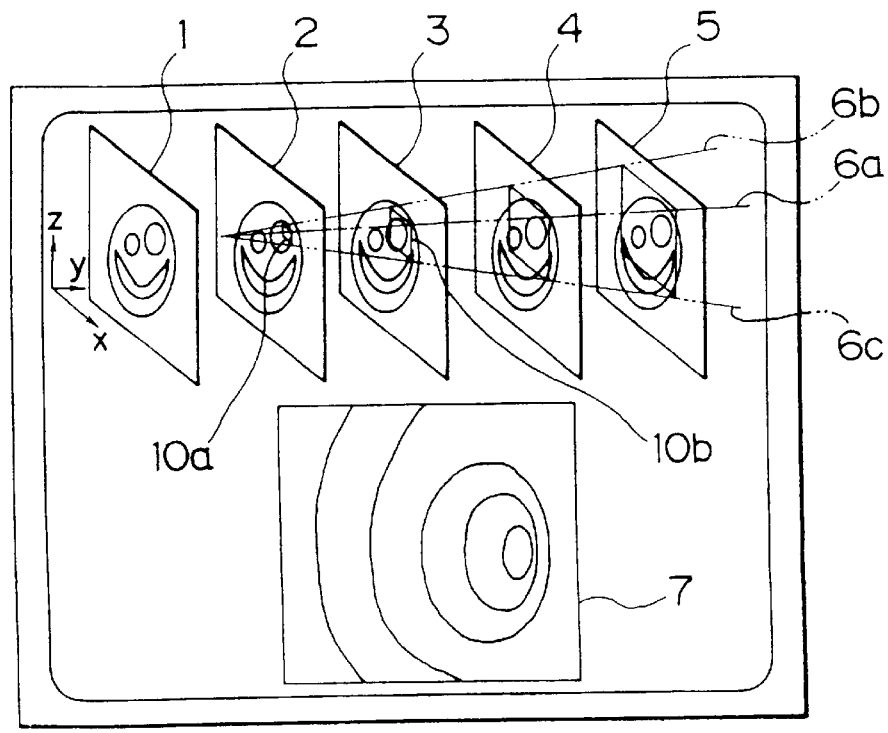

FIG. 1(a) illustrates the first embodiment of a display image, which is displayed on the CRT monitor 54 by the CPU 50.

As shown in FIG. 1(a), a three-dimensional image 7, which is obtained by seeing the organ from the inside, is displayed at the lower part of the display screen. The three-dimensional image 7 is formed in the central projection method described in FIGS. 6, 7, and 8.

A plurality of tomographic images 1, 2, 3, 4, and 5 are displayed at the upper part of the display screen. These tomographic images are extracted at regular intervals from the tomographic images interposed between a point behind the viewpoint $\underline{e}$ and the projection plane. These tomographic images are formed and displayed according to the CT data stored in the magnetic disk 52. Polygon visual field frames such as squares 10, 11, 12, and 13 are displayed on the tomographic images 2, 3, 4, and 5, respectively, along the line of sight D from the viewpoint $\underline{e}$. The square visual field frames are constructed along lines of intersection of the projection lines at the outermost of plural projection lines forming a quadrangular pyramid and the tomographic images. (That is, the visual field frame is a square whose vertexes are four points of intersection of the tomographic images and projection lines from the viewpoint $\underline{e}$ toward four corners K1, K2, K3, and K4 of the projection plane in FIG. 8.)

If the position of the viewpoint $\underline{e}$ and the line of sight D of the three-dimensional image 7 are moved, the three-dimensional image 7 and the tomographic images 1, 2, 3, 4, and 5 are sequentially updated. In this case, the corresponding CT data are read out from the magnetic disk 52, so that the images can be formed and displayed. The three-dimensional image 7 and the tomographic images 1 through 5 may be switched and selectively displayed on the display screen.

As stated above, the visual field frame of the three-dimensional image 7, which is viewed from the inside of the organ, is displayed on the tomographic image at the upper part of the screen, so that the position of the viewpoint e and the line of sight D can be easily recognized.

FIG. 1(b) illustrates the second embodiment of the display image shown on the CRT monitor 54. The display image in FIG. 1(b) shows the inclined front view of the tomographic image in FIG. 1(a). That is, the tomographic images 1, 2, 3, 4, and 5 are displayed at the upper part of the display screen. In this case, the tomographic images, which show the inclined front views of the diagonally-warped tomographic images, are displayed at the upper part of the display screen.

If unit vectors in the direction of the x and z axes projected on the projection plane are referred to as i and j, and the coordinates of a point on the image, not warped, are referred to as (A, B), the coordinates of a pixel point on the diagonally-warped image are (Ai, Bj). In this case, the CT data are read out from the magnetic disk 52, and the CPU 50 computes the CT data.

As shown in FIG. 1(b), projection lines 6a, 6b, and 6c at the outermost of the projection lines forming the quadrangular pyramid may be displayed on the tomographic images 1, 2, 3, 4 and 5.

Figure 2:
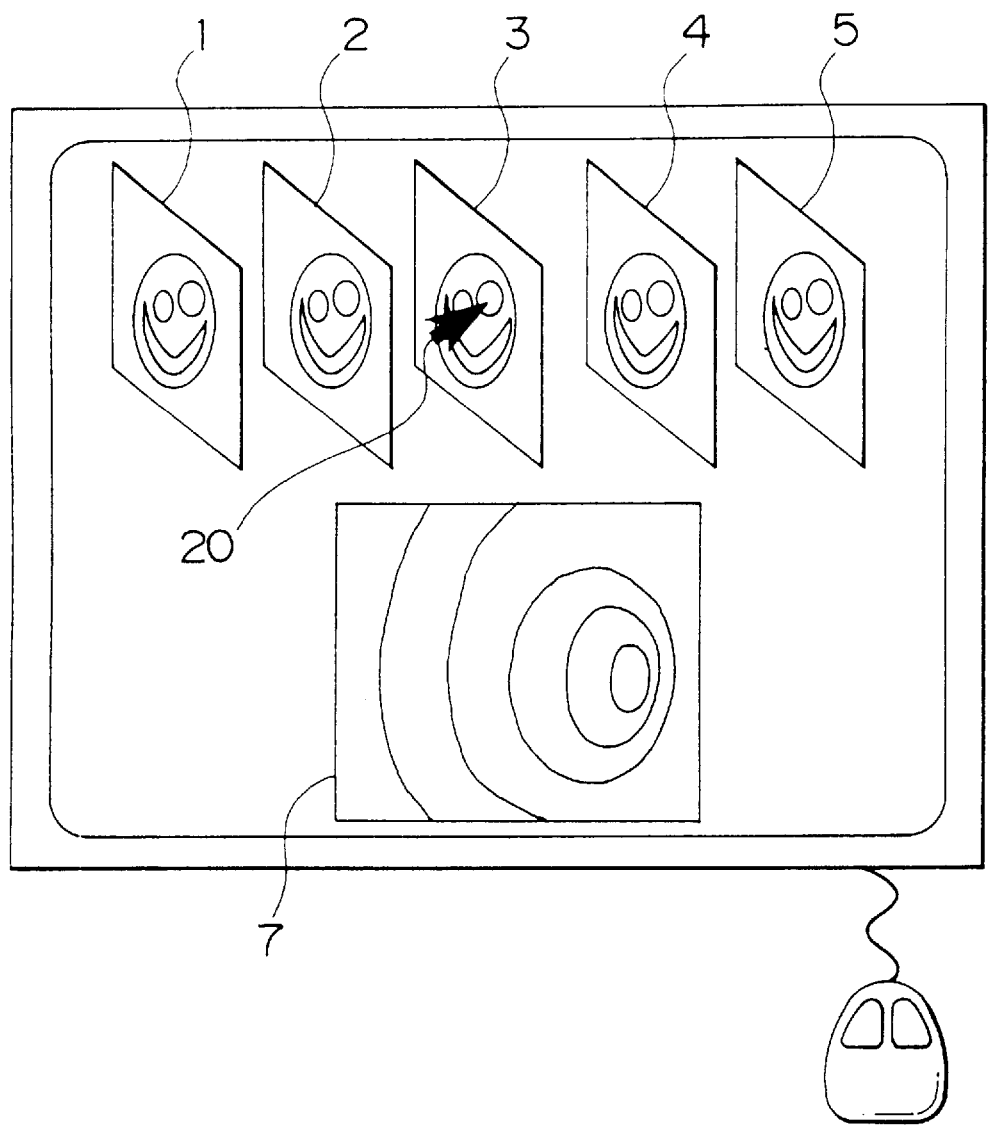
FIG. 2 is a view showing a relationship between a three-dimensional image and a viewpoint (marker) displayed on a tomographic image.
Figure 3:
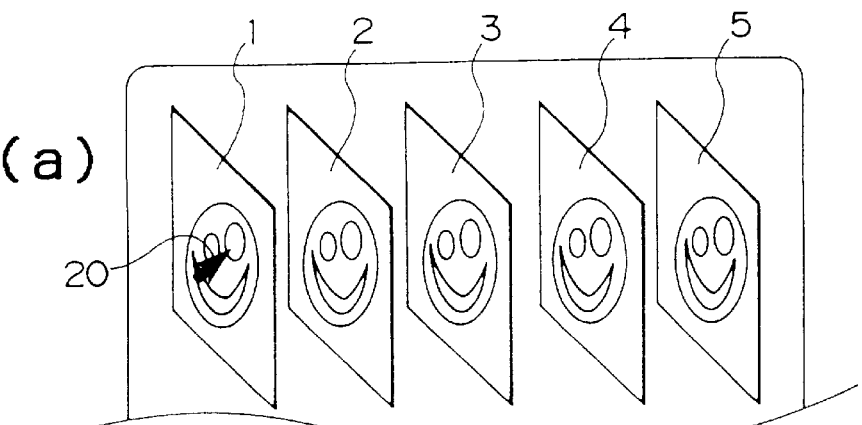
FIGS. 3(a), 3(b) and 3(c) are segmentary views of the viewpoint (marker) on the tomographic image being moved in FIG. 2.
Figure 3:
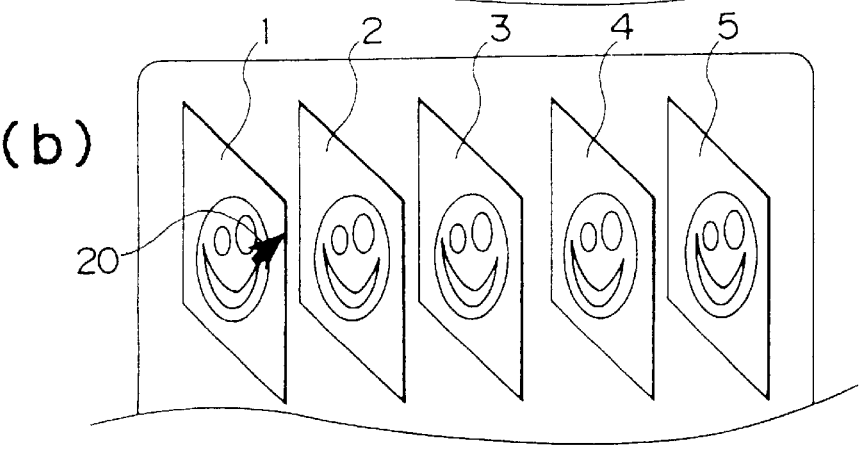
Figure 3:
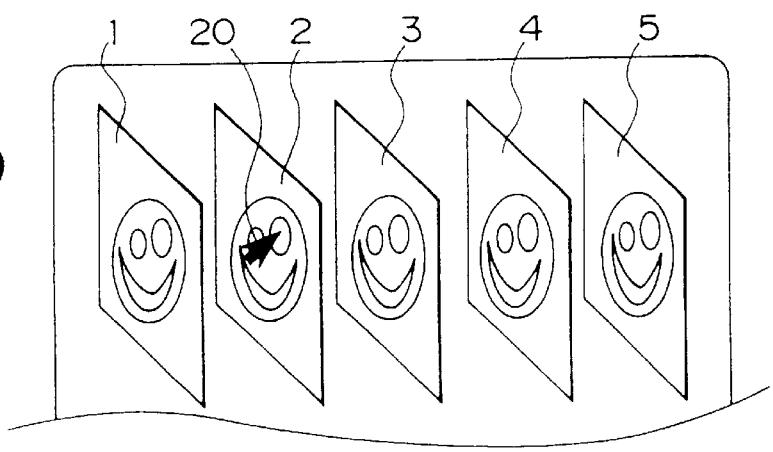

FIGS. 2, 3(a), 3(b), and 3(c) illustrate the third embodiment of images displayed on the CRT monitor 54. In FIG. 2, as is the case with the images shown in FIG. 1(b), the three-dimensional image 7 is displayed at the lower part of the display screen, and the diagonally-warped tomographic images 1, 2, 3, 4, and 5 are displayed at the upper part of the display screen (the tomographic images may be displayed as the front views as shown in FIG. 1(a)). A marker 20 is displayed at one position on the tomographic image correspondingly to the position of the viewpoint e with respect to the three-dimensional image 7. When the viewpoint e of the three-dimensional image 7 moves, the marker 20 moves in connection with the movement of the viewpoint e as shown in FIGS. 3(a), (b) and (c).

As stated above, the position of the viewpoint e of the three-dimensional image may be displayed by the marker 20. In this case, the CPU 50 computes the coordinates of the viewpoint e projected on the projection plane, and the marker 20 is displayed at the position of the coordinates. In general, the viewpoint e is located halfway between the tomographic images, and the marker 20 indicating the viewpoint e may be displayed on every tomographic image. In order to simplify the display, however, the marker 20 may be displayed only on the tomographic image closest to the viewpoint e. The line of sight may also be indicated as the direction pointed by the marker 20.

Figure 4:
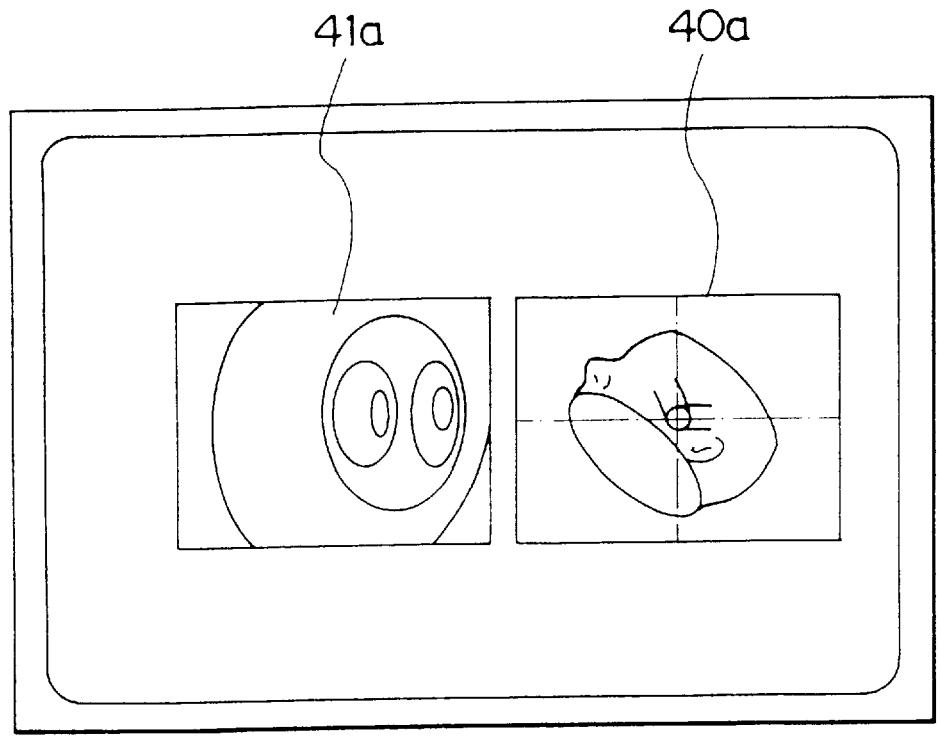
FIGS. 4(a) and 4(b) are views showing a relationship between a three-dimensional image showing the inside of an object and a three-dimensional image showing the whole object which is observed from the viewpoint moving backward.
Figure 4:
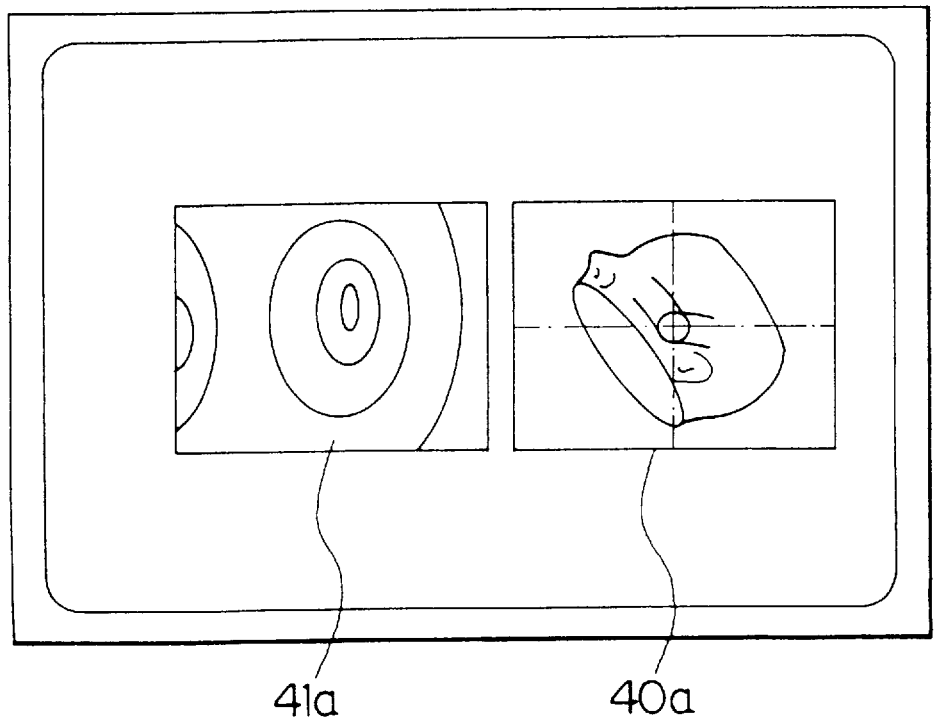

FIGS. 4(a) and 4(b) illustrate the forth embodiment of images displayed on the CRT monitor 54. A three-dimensional image 41a, which is constructed by setting the viewpoint e and the line of sight D in the inside of the object, is displayed at the left of the display screen in FIG. 4(a).

A three-dimensional image 40a is displayed at the right of the screen. The three-dimensional image 40a is constructed by setting the same line of sight D as that of the three-dimensional image 41a and placing a viewpoint behind the viewpoint e along the line of sight D of the three-dimensional image 41a (for example, at a position where the shape of the whole object can be recognized with a person's eyes).

Thereby, the position of the viewpoint e of the three-dimensional image 41a, which viewpoint is placed in the object, is displayed at the center of the three-dimensional image 40a. In this case, the line of sight D is vertical to the screen.

FIG. 4(b) describes the case where the line of sight in FIG. 4(a) is changed. In the above-stated processing, the CT data are read out from the magnetic disk 52, so that the images can be formed and displayed. All images may be constructed in the central projection method described in FIGS. 6, 7 and 8.

Thus, the viewpoint e of the three-dimensional image 41a in the object is indicated by a central position of the three-dimensional image 40a showing the whole object (a position where the alternate long and short dash lines cross each other).

The three-dimensional images 41a and 40a may be switched and selectively displayed on the display screen as shown in FIG. 5.

As set forth hereinabove, in the method and apparatus for displaying the three-dimensional image of the present invention, the part of the organ which is being displayed can be indicated when the three-dimensional image is displayed as if it was observed under the endoscope, and the positional relationship between the entire organ and the display position can be easily recognized.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A method of displaying a three-dimensional image, comprising the steps of:

forming a first image, the first image including the three-dimensional image formed from a first plurality of tomographic images;

forming a second image, the second image including a second plurality of tomographic images that include at least one of the first plurality of tomographic images; and displaying at least one of the first and second images.

2. The method of claim 1, wherein the first plurality of tomographic images include a volume image.

3. The method of claim 1, further comprising shading the three-dimensional image.

4. The method of claim 1, wherein the displaying step displays the first and the second images concurrently.

5. The method of claim 1, wherein the displaying step displays either the first image or the second image and permits switching between the first and the second images.

6. The method of claim 1, wherein the second plurality of tomographic images are sequentially arranged in the second image.

7. The method of claim 1, wherein the second plurality of tomographic images are diagonally warped and inclined in the second image.

8. The method of claim 1, wherein the first plurality of tomographic images are stacked to form the three-dimensional image projected onto. a projection plane from a viewpoint in a direction of a line of sight extending from the viewpoint toward the projection plane.

9. The method of claim 8, wherein the second plurality of tomographic images further include at least one tomographic image behind the viewpoint relative to the line of sight and the projection plane.

10. The method of claim 8, wherein the first and the second images are reformed when one of a position of the viewpoint and the direction of the line of sight is changed.

11. The method of claim 10, wherein the second plurality of tomographic images are diagonally warped and inclined in the second image.

12. The method of claim 8, wherein information corresponding to at least one of a position of the viewpoint and the direction of the line of sight is added to the second image.

13. The method of claim 12, further comprising determining a plurality of projection lines between the viewpoint and the projection plane, each of the projection lines having a same preset angle relative to the line of sight, wherein the information comprises polygons, each of the polygons corresponding to one of the first plurality of tomographic images, sides of the polygons being formed by connecting intersecting positions between the projection lines and a plane corresponding to the one of the first plurality of tomographic images.

14. The method of claim 12, wherein the information comprises either an indication of the position of the viewpoint within one of the second plurality of tomographic images or a marker placed in a position on one of the second plurality of tomographic images that is closest to the position of the viewpoint.

15. The method of claim 14, wherein the second plurality of tomographic images are diagonally warped and inclined in the second image.

16. The method of claim 13, wherein the polygons corresponding to the first plurality of tomographic images are squares, the squares forming a pyramid.

17. The method of claim 16, wherein the second plurality of tomographic images are diagonally warped and inclined in the second image.

18. A method of displaying a three-dimensional image of an object, comprising the steps of:

forming a first image, the first image including a first pseudo three-dimensional image formed from a first plurality of tomographic images;

forming a second image, the second image including a second pseudo three-dimensional image formed from a second plurality of tomographic images including at least one of the first plurality of tomographic images; and displaying at least one of the first and the second images.

19. The method of claim 18, wherein the first plurality of tomographic images include a volume image.

20. The method of claim 18, wherein the displaying step displays either the first and the second images concurrently or one of the first and the second images, when displaying one of the first and the second images, the displaying step permitting switching between the first and the second images.

21. The method of claim 18, further comprising the step of shading the first and second pseudo three-dimensional images.

22. The method of claim 18, wherein the second pseudo three-dimensional image represents the object as a whole.

23. The method of claim 18, wherein:

the first plurality of tomographic images are stacked to form the first pseudo three-dimensional image projected onto a first projection plane from a first viewpoint in a direction of a line of sight extending from the first viewpoint toward the first projection plane; and the second plurality of tomographic images are stacked to form the second pseudo three-dimensional image projected onto a second projection plane from a second viewpoint in the direction of the line of sight.

24. The method of claim 23, wherein the second viewpoint is behind the first viewpoint relative to the first projection plane.

25. The method of claim 23, wherein the first and second images are reformed when one of a position of the first viewpoint, a position of the second viewpoint and the direction of the line of sight is changed.

26. The method of claim 23, wherein information corresponding to at least one of a position of the first viewpoint and the direction of the line of sight is added to the second image.

27. An apparatus that displays a three-dimensional image of an object, comprising:

first image constructing means for constructing a first image, the first image including the three-dimensional image formed from a first plurality of tomographic images;

second image constructing means for constructing a second image, the second image including a second plurality of tomographic images that include at least one of the first plurality of tomographic images; and image displaying means for displaying at least one of the first and second images.

28. The apparatus of claim 27, wherein the first plurality of tomographic images include a volume image.

29. The apparatus of claim 27, wherein the first image constructing means shades the three-dimensional image.

30. The apparatus of claim 27, wherein the image displaying means displays the first and the second images concurrently.

31. The apparatus of claim 27, wherein the image displaying means displays either the first image or the second image and permits switching between the first and the second images.

32. The apparatus of claim 27, wherein the second image constructing means diagonally warps and inclines the second plurality of tomographic images in the second image.

33. The apparatus of claim 27, wherein:

the first image constructing means stacks the first plurality of tomographic images to form the three-dimensional image projected onto a projection plane from a viewpoint in a direction of a line of sight extending from the viewpoint toward the projection plane; and the second image constructing means adds information corresponding to at least one of a position of the viewpoint and the direction of the line of sight to the second image.

34. The apparatus of claim 27, wherein the second image constructing means sequentially arranges the second plurality of tomographic images in the second image.

35. An apparatus for displaying a three-dimensional image of an object, comprising:

first image constructing means for constructing a first image, the first image including a first pseudo three-dimensional image formed from a first plurality of tomographic images;

second image constructing means for constructing a second image, the second image including a second pseudo three-dimensional image formed from a second plurality of tomographic images including at least one of the first plurality of tomographic images; and image displaying means for displaying at least one of the first and the second images.

36. The apparatus of claim 35, wherein the first plurality of tomographic images include a volume image.

37. The apparatus of claim 35, wherein the image displaying means displays either the first and the second images concurrently or one of the first and the second images, when displaying one of the first and the second images, the image displaying means permitting switching between the first and the second images.

38. The apparatus of claim 35, wherein:
the first image constructing means stacks the first plurality of tomographic images to form the first pseudo three-dimensional image projected onto a first projection plane from a first viewpoint in a direction of a line of sight extending from the first viewpoint toward the first projection plane; and the second image constructing means stacks the second plurality of tomographic images to form the second pseudo three-dimensional image projected onto a second projection plane from a second viewpoint in the direction of the line of sight and adds information corresponding to at least one of a position of the first viewpoint and the direction of the line of sight to the second image.

39. The apparatus of claim 35, wherein the second pseudo three-dimensional image represents the object as a whole.

40. A method of displaying a three-dimensional image, comprising the steps of:

forming a first image, the first image including the three-dimensional image formed from predetermined areas of a first plurality of tomographic images, each of the predetermined areas being extracted from each of the first plurality of tomographic images, the predetermined areas being different from one another in size;

forming a second image, the second image including a second plurality of tomographic images that include at least one of the first plurality of tomographic images; and displaying at least one of the first and second images.

41. The method of claim 40, wherein the predetermined areas of the first plurality of tomographic images are polygons similar to one another.

42. The apparatus of claim 40, wherein the second plurality of tomographic images further include at least one tomographic image behind the viewpoint relative to the line of sight and the projection plane.

43. The method of claim 40, wherein the second plurality of tomographic images are sequentially arranged in the second image.

44. The method of claim 43, wherein the second plurality of tomographic images are diagonally warped and inclined in the second image.

45. The method of claim 43, wherein information corresponding to the predetermined area in said at least one of the first plurality of tomographic images included in the second image is added to said at least one of the first plurality of tomographic images in the second image.

46. The method of claim 44, wherein:
the predetermined areas of the first plurality of tomographic images are stacked to form the three-dimensional image projected onto a projection plane from a viewpoint in a direction of a line of sight extending from the viewpoint toward the projection plane; and information corresponding to at least one of the viewpoint, the predetermined area in said at least one of the first plurality of tomographic images included in the second image, and at least one projection line connecting the viewpoint and the projection plane and passing through sides of the predetermined areas of the first plurality of tomographic images is added to the second image.

47. An apparatus for displaying a three-dimensional image of an object, comprising:

first image constructing means for constructing a first image, the first image including the three-dimensional image formed from predetermined areas of a first plurality of tomographic images, each of the predetermined areas being extracted from each of the first plurality of tomographic images, the predetermined areas being different from one another in size;

second image constructing means for constructing a second image, the second image including a second plurality of tomographic images that include at least one of the first plurality of tomographic images; and image displaying means for displaying at least one of the first and second images.

48. The apparatus of claim 47, wherein the second image constructing means sequentially arranges the second plurality of tomographic images in the second image and adds information corresponding to the predetermined area in said at least one of the first plurality of tomographic images included in the second image to said at least one of the first plurality of tomographic images in the second image.

49. The apparatus of claim 47, wherein:
the first image constructing means stacks the predetermined areas of the first plurality of tomographic images to form the three-dimensional image projected onto a projection plane from a viewpoint in a direction of a line of sight extending from the viewpoint toward the projection plane;

the second image constructing means diagonally warps and inclines the second plurality of tomographic images, sequentially arranges the warped and inclined second plurality of tomographic images in the second image, and adds information corresponding to at least one of the viewpoint, the predetermined area in said at least one of the first plurality of tomographic images included in the second image, and at least one projection line connecting the viewpoint and the projection plane and passing through sides of the predetermined areas of the first plurality of tomographic images to the second image.

50. An apparatus for displaying a three-dimensional image, comprising:

storage for storing first and second images, the first image including the three-dimensional image formed from a first plurality of tomographic images, the second image being formed from a second plurality of tomographic images including at least one of the first plurality of tomographic images;

a controller for receiving a command to retrieve at least one of the first and second images from the storage; and a display coupled to the controller for displaying the image retrieved from the storage in accordance with the command received by the controller.

51. The apparatus of claim 50, further comprising:
a data bus for connecting the storage, the controller and the display with one another, data being channeled between the storage, the controller and the display through the data bus.

52. The apparatus of claim 50, wherein:
the storage stores the first image including the three-dimensional image formed by stacking the first plurality of tomographic images, the three-dimensional image being projected onto a projection plane from a viewpoint in a direction of a line of sight extending from the viewpoint toward the projection plane, and the storage stores the second image in which the second plurality of tomographic images are sequentially arranged;

the controller receives one of a command to display either the first and second images concurrently, and a command to display one of the first and second images while permitting switching between the first and second images; and the display displays either the first and second images concurrently or one of the first and second images while permitting switching between the first and second images in accordance with the command received by the controller.

53. The apparatus of claim 50, wherein:

the storage stores the three-dimensional image being a first three-dimensional image formed by stacking the first plurality of tomographic images, the first three-dimensional image being projected onto a first projection plane from a first viewpoint in a direction of a line of sight extending from the first viewpoint toward the first projection plane, and the storage stores the second image including a second three-dimensional image formed by stacking the second plurality of tomographic images, the second three-dimensional image being projected onto a second projection plane from a second viewpoint in the direction of the line of sight;

the controller receives one of a command to display either the first and second images concurrently, and a command to display one of the first and second images while permitting switching between the first and second images; and the display displays either the first and second images concurrently or one of the first and second images while permitting switching between the first and second images in accordance with the command received by the controller.

54. The apparatus of claim 52, wherein:

the storage stores the first image including the three-dimensional image formed from predetermined areas of the first plurality of tomographic images, each of the predetermined areas being extracted from each of the first plurality of tomographic images, the predetermined areas being similar to one another, and the storage stores information corresponding to the predetermined area of said at least one of the first plurality of tomographic images included in the second image;

the controller receives a command to add the information to said at least one of the first plurality of tomographic images in the second image; and the display displays the second image added with the information in accordance with the command received by the controller.

55. An X-ray computerized tomography (CT) apparatus that produces a plurality of CT images of preferred slices of an object, the X-ray CT apparatus comprising:

storage for storing first and second images, the first image including a three-dimensional image formed from a first plurality of CT images, the second image being formed from a second plurality of CT images including at least one of the first plurality of CT images;

a controller for receiving a command to retrieve at least one of the first and second images from the storage; and a display coupled to the controller for displaying the image retrieved from the storage in accordance with the command received by the controller.

56. The apparatus of claim 55, further comprising:

a data bus for connecting the storage, the controller and the display with one another, data being channeled between the storage, the controller and the display through the data bus.

57. A magnetic resonance (MR) imaging apparatus that produces a plurality of MR images of preferred slices or a volume image of an object, the plurality of MR images in a predetermined field being three-dimensionally arranged in the volume image, the MR imaging apparatus comprising:

storage for storing first and second images, the first image including a three-dimensional image formed from a first plurality of MR images or a first volume image, the second image being formed from a second plurality of MR images or a second volume image including at least one of the first plurality of MR images or the first volume image;

a controller for receiving a command to retrieve at least one of the first and second images from the storage; and a display coupled to the controller for displaying the image retrieved from the storage in accordance with the command received by the controller.

58. The apparatus of claim 57, further comprising:

a data bus for connecting the storage, the controller and the display with one another, data being channeled between the storage, the controller and the display through the data bus.

* * * * *